United States Patent [19]

Tomcufcik et al.

[11] Patent Number: 4,576,943

[45] Date of Patent: Mar. 18, 1986

[54] PYRAZOLO[1,5-a]PYRIMIDINES

[75] Inventors: Andrew S. Tomcufcik, Old Tappan, N.J.; Walter E. Meyer, Suffern; John P. Dusza, Nanuet, both of N.Y.; Shin S. Tseng, Bridgewater, N.J.

[73] Assignee: American Cyanamid Company, Stamford, Conn.

[21] Appl. No.: 659,069

[22] Filed: Oct. 9, 1984

[51] Int. Cl.[4] .............. A61K 31/505; A61K 31/535; A61K 31/54; C07D 471/04
[52] U.S. Cl. .................... 514/222; 514/234; 514/237; 514/258; 544/58.6; 544/59; 544/60; 544/61; 544/117; 544/140; 544/159; 544/281; 544/360; 544/364; 544/371; 544/379; 544/394; 544/398; 546/211; 546/230; 546/246

[58] Field of Search ............... 544/58.6, 61, 117, 281; 514/222, 231, 237, 258

[56] References Cited

U.S. PATENT DOCUMENTS 4,178,449  12/1979  Dusza et al. .................. 544/281
4,281,000   7/1981  Dusza et al. .................. 544/281 X

*Primary Examiner*—Richard L. Raymond
*Attorney, Agent, or Firm*—Edward A. Conroy, Jr.

[57] ABSTRACT

This disclosure describes certain pyrazolo[1,5-a]pyrimidines useful as hypotensive and/or anxiolytic agents, or as agents for the treatment of cognitive and related neural behavioral problems in mammals.

22 Claims, No Drawings

PYRAZOLO[1,5-a]PYRIMIDINES

BRIEF SUMMARY OF THE INVENTION

This invention relates to new organic compounds and, more particularly, is concerned with novel pyrazolo[1,5-a]pyrimidines which are useful as hypotensive agents and some of which are also useful as anxiolytic agents or as agents for the treatment of cognitive and related neural behavioral problems in mammals. The novel compounds of the present invention may be represented by the following structural formula:

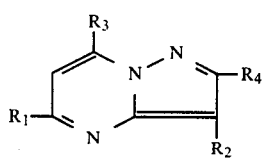
(I)

wherein $R_1$ is hydrogen, methyl or trifluoromethyl; $R_2$ is cyano, carbamoyl or a moiety of the formula:

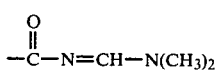

$R_3$ is phenyl, 3-chlorophenyl, 4-chlorophenyl, 3-(trifluoromethyl)phenyl, 3-pyridyl or 4-pyridyl; and $R_4$ is 1-piperidino, 4-benzyl-1-piperidino, 4-morpholino, 4-thiomorpholino or a moiety of the formula:

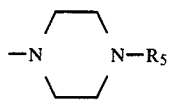

wherein $R_5$ is methyl, phenyl, 2-pyridyl, 2-furanylmethyl, 3-phenyl-2-propenyl, benzyl, 3-chlorobenzyl, 4-chlorobenzyl, 3,4-dichlorobenzyl, 2,6-dichlorobenzyl, 3-methoxybenzyl, 4-methoxybenzyl, β-hydroxyethyl, 2-phenoxyethyl, 3-phenoxypropyl or 4-phenoxylbutyl; and the pharmacologically acceptable acid-addition salts thereof.

This invention also includes novel compositions of matter containing the above-defined compounds which are useful as hypotensive and/or anxiolytic agents and as agents for the treatment of cognitive and related neural behavioral problems in mammals and the methods for treating hypertension and/or anxiety and neural behavioral problems in mammals therewith.

DETAILED DESCRIPTION OF THE INVENTION

The novel compounds of the present invention are, in general, obtainable as pale yellow, yellow or tan crystalline solids having characteristic melting points and absorption spectra. They are appreciably soluble in many organic solvents such as lower alkanols, chloroform, dichloromethane, tetrahydrofuran, acetone, N,N-dimethylformamide, and the like, but are relatively insoluble in water. These compounds are organic bases and thus are capable of forming acid-addition salts with a variety of organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene and the like. For purposes of this invention the free bases are equivalent to their non-toxic acid-addition salts.

The novel pyrazol[1,5-a]pyrimidine compounds of present invention may be readily prepared as set forth in the following reaction schemes wherein $R_1$ and $R_3$ are as hereinabove defined and X is a moiety of the formulae:

$$>O, >S, >CH_2, >CH\text{-benzyl or} >N-R_5$$

wherein $R_5$ is as hereinbefore defined.

SCHEME A

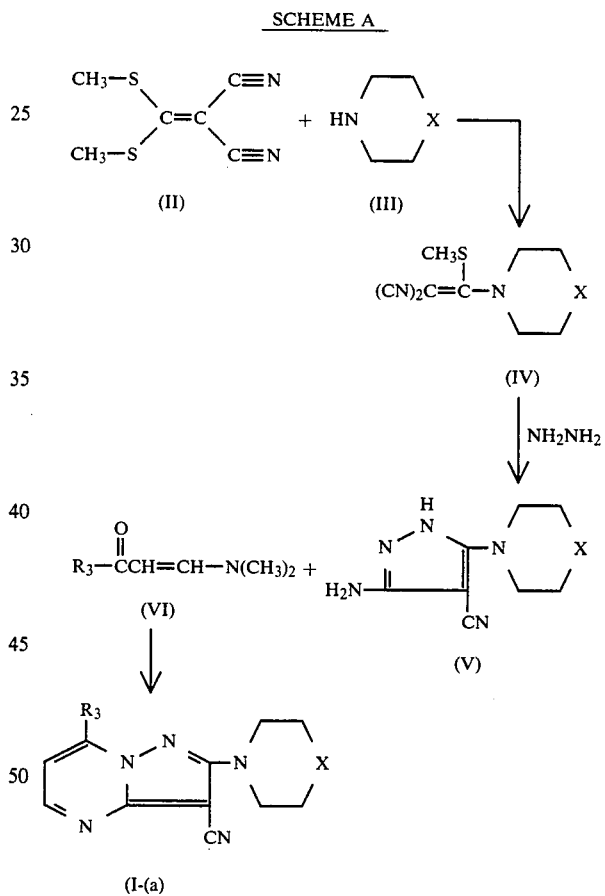

In accordance with the above reaction sequence, [bis(methylthio)methylene]malononitrile (II) and a compound (III) where X is as hereinabove described, are refluxed in acetonitrile, ethanol or a similar solvent for 2–20 hours, giving a solution of a compound described by the chemical structure (IV) which is then refluxed with hydrazine hydrate in the solvent for 1–18 hours to provide the desired pyrazole intermediate compound (V). The intermediate (V) is reacted with a 3-dimethylamino-1-(aryl, substituted aryl or heteroaryl)-2-propen-1-one (VI) in refluxing glacial acetic acid for 1–20 hours to provide the product (Ia) of the invention which is collected and purified in a conventional manner.

The novel compounds of the present invention where $R_1$ in structural formula (I) may be other than hydrogen, may be prepared as shown in reaction Scheme B below:

SCHEME B

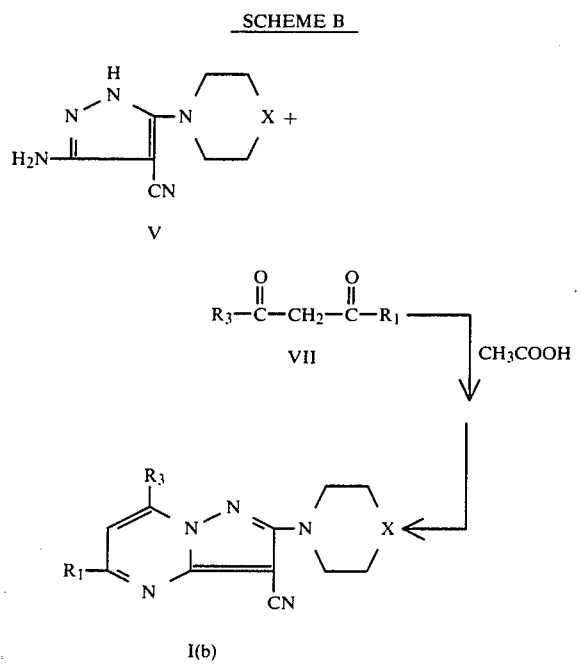

wherein $R_1$ is methyl or trifluoromethyl, $R_3$ is phenyl or 4-pyridyl, and X is >N-benzyl.

In accordance with reaction sequence B, an appropriate pyrazole compound (V) is reacted with a β-diketone (VII) such as 4,4,4-trifluoro-1-(4-pyridyl)-1,3-butanedione, 1-benzoylacetone, or 1-(4-pyridyl)-1,3-butanedione and the like in refluxing glacial acetic acid for 2–20 hours giving the products (Ib) of the invention.

The novel compounds of the present invention where $R_2$ is carbamoyl in structural formula (I) may be obtained by acid hydrolysis of the product (I) where $R_2$ is cyano, by stirring with concentrated sulfuric acid for 2–6 hours.

When the above amide is heated with N,N-dimethylformamide dimethyl acetal at 120°–130° C. for 2–6 hours the derivative where $R_2$ is —CO—N=CH—N(CH$_3$)$_2$ is obtained.

The novel compounds of the present invention are active hypotensive agents and were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y., having an average mean arterial blood pressure of 170±1.5 mm of mercury are used in the test. One to 3 rats are used per test compound. A rat is dosed by gavage with a test compound suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin (see above). The procedure is repeated in a second and third rat when necessary.

The results of this test on representative compounds of the present invention which were obtained using one or two rats, at a dose of 100 mg/kg of body weight appear below in Table I.

TABLE I

| Hypotensive Activity In Spontaneously Hypertensive Rats | |
|---|---|
| Compound | Mean Arterial Blood Pressure (mm of mercury) |
| 2-(4-Phenylmethyl-1-piperazinyl)-7-(4-pyridinyl)pyrazolo[1,5-a]pyrimidine-3-carbonitrile | 90 123 |
| 2-[4-[(3,4-Dichlorophenyl)methyl]-1-piperazinyl]-7-(4-pyridinyl)pyrazolo-[1,5-a]pyrimidine-3-carbonitrile | 118 117 |
| 2-[4-(Phenylmethyl)-1-piperazinyl]-7-(3-pyridinyl)pyrazolo[1,5-a]pyrimidine-3-carbonitrile | 124 124 |
| 2-[4-(Phenylmethyl)-1-piperazinyl]-7-[3-(trifluoromethyl)phenyl]pyrazolo[1,5-a]-pyrimidine-3-carbonitrile | 115 132 |
| 2-[4-(Phenylmethyl)-1-piperazinyl]-7-(4-pyridinyl)pyrazolo[1,5-a]pyrimidine-3-carboxamide | 120 108 |
| 2-[4-(Phenylmethyl)-1-piperazinyl]-7-(4-pyridinyl)-5-(trifluoromethyl)pyrazolo-[1,5-a]pyrimidine-3-carbonitrile | 111 117 |
| 2-[4-(3-Phenoxypropyl)-1-piperazinyl]-7-(4-pyridinyl)pyrazolo[1,5-a]pyrimidine-3-carbonitrile | 143 144 |
| 2-[4-(2-Phenoxyethyl)-1-piperazinyl]-7-(4-pyridinyl)pyrazolo[1,5-a]pyrimidine-3-carbonitrile | 137 116 |
| 2-[4-(2-Furanylmethyl)-1-piperazinyl]-7-(4-pyridinyl)pyrazolo[1,5-a]pyrimidine-3-carbonitrile | 104 118 |
| 5-Methyl-2-[4-(phenylmethyl)-1-piperazinyl]-7-(4-pyridinyl)pyrazolo[1,5-a]-pyrimidine-3-carbonitrile | 122 122 |
| 2-[4-(3-Phenyl-2-propenyl)-1-piperazinyl]-7-(4-pyridinyl)pyrazolo[1,5-a]pyrimidine-3-carbonitrile | 136 140 |
| 2-(4-Morpholinyl)-7-[3-(trifluoromethyl)phenyl]pyrazolo[1,5-a]pyrimidine-3-carbonitrile | 142 |
| 2-(4-Methyl-1-piperazinyl)-7-[3-(trifluoromethyl)phenyl]pyrazolo[1,5-a]-pyrimidine-3-carbonitrile | 139 |
| 7-(4-Chlorophenyl)-2-[4-(phenylmethyl)-1-piperazinyl]pyrazolo[1,5-a]pyrimidine-3-carbonitrile | 142 |
| 5-Methyl-7-phenyl-2-[4-(phenylmethyl)-1-piperazinyl]pyrazolo[1,5-a]pyrimidine-3-carbonitrile | 131 |
| 7-(3-Chlorophenyl)-2-[4-(phenylmethyl)-1-piperazinyl]pyrazolo[1,5-a]pyrimidine-3-carbonitrile | 147 |
| 2-[4-(4-Phenoxybutyl)-1-piperazinyl]-7-[3-(trifluoromethyl)phenyl]pyrazolo[1,5-a]-pyrimidine-3-carbonitrile | 147 |
| 2-(4-Thiomorpholinyl)-7-[3-(trifluoromethyl)phenyl]pyrazolo[1,5-a]pyrimidine-3-carbonitrile | 148 |
| 2-[4-(2-Hydroxyethyl)-1-piperazinyl]-7-[3-(trifluoromethyl)phenyl]pyrazolo-[1,5-a]pyrimidine-3-carbonitrile | 111 |
| 7-(3-Pyridinyl)-2-[4-(2-pyridinyl)-1-piperazinyl]pyrazolo[1,5-a]pyrimidine-3-carbonitrile | 143 |
| 2-(1-Piperidinyl)-7-(3-pyridinyl)pyrazolo-[1,5-a]pyrimidine-3-carbonitrile | 141 |
| 2-[4-(4-Phenoxybutyl)-1-piperazinyl]-7-(3-pyridinyl)pyrazolo[1,5-a]pyrimidine-3-carbonitrile | 144 |
| 7-(3-Pyridinyl)-2-(4-thiomorpholinyl)-pyrazolo[1,5-a]pyrimidine-3-carbonitrile | 141 |
| 2-[4-(Phenylmethyl)-1-piperazinyl]-7-[3-(trifluoromethyl)phenyl]pyrazolo[1,5-a]-pyrimidine-3-carboxamide | 126 111 |

TABLE I-continued

Hypotensive Activity In Spontaneously Hypertensive Rats

| Compound | Mean Arterial Blood Pressure (mm of mercury) |
|---|---|
| N—[(Dimethylamino)methylene]-2-[4-(phenylmethyl)-1-piperazinyl]-7-[3-(trifluoromethyl)phenyl]pyrazolo[1,5-a]pyrimidine-3-carboxamide | 103 |
| 2-[4-(Phenylmethyl)-1-piperidinyl]-7-[3-(trifluoromethyl)phenyl]pyrazolo[1,5-a]pyrimidine-3-carbonitrile | 142 |
| 2-[4-[(3-Chlorophenyl)methyl]-1-piperazinyl]-7-(3-pyridinyl)pyrazolo[1,5-a]pyrimidine-3-carbonitrile | 137 |
| 2-[4-[(4-Methoxyphenyl)methyl]-1-piperazinyl]-7-[3-(trifluoromethyl)phenyl]pyrazolo[1,5-a]pyrimidine-3-carbonitrile | 136 |
| 2-[4-[(4-Chlorophenyl)methyl]-1-piperazinyl]-7-(3-pyridinyl)pyrazolo[1,5-a]pyrimidine-3-carbonitrile | 137 |
| 2-[4-[(4-Chlorophenyl)methyl]-1-piperazinyl]-7-[3-(trifluoromethyl)phenyl]pyrazolo[1,5-a]pyrimidine-3-carbonitrile | 127 |
| 2-[4-[(3-Methoxyphenyl)methyl]-1-piperazinyl]-7-(3-pyridinyl)pyrazolo[1,5-a]pyrimidine-3-carbonitrile | 138 |
| 2-[4-[(3-Methoxyphenyl)methyl]-1-piperazinyl]-7-[3-(trifluoromethyl)phenyl]pyrazolo[1,5-a]pyrimidine-3-carbonitrile | 140 |
| 2-[4-[(2,6-Dichlorophenyl)methyl]-1-piperazinyl]-7-(3-pyridinyl)pyrazolo[1,5-a]pyrimidine-3-carbonitrile | 124 |
| 2-[4-[(3-Chlorophenyl)methyl]-1-piperazinyl]-7-phenylpyrazolo[1,5-a]pyrimidine-3-carbonitrile | 135 139 |
| 2-[4-[(2,6-Dichlorophenyl)methyl]-1-piperazinyl]-7-(4-pyridinyl)pyrazolo[1,5-a]pyrimidine-3-carbonitrile | 122 117 |

Certain of the novel compounds of the present invention possess central nervous system activity at non-toxic doses and as such are useful as anxiolytic agents; that is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The antianxiety effects of the novel compounds of the present invention have been assessd in a non-conditioned passive avoidance procedure described by J. R. Vogel, B. Beer and D. E. Clody, "A Simple and Reliable Conflict Procedure for Testing Antianxiety Agents", Psychopharmacologia, 21, 1–7 (1971). A conflict situation was induced in rats by a modification of this method.

Groups of 6 naive, Wistar strain rats, weighing 200–240 g each, were deprived of water for 48 hours and food for 24 hours. The test compounds were administered in single or graded, oral or intraperitoneal doses, suspended in a 2% starch vehicle containing 0.5% v/v polyethylene glycol and one drop of Polysorbate 80. Control animals received the vehicle alone. At 30 or 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group.

The test compounds are considered active if the number of shocks received by the test group is significantly higher than the control group by the Mann-Witney U test.

The results of this test on representative compounds of this invention appear in Table II.

TABLE II

Non-Conditioned Passive Avoidance Test in Rats

| Compound | Dose mg/kg | Result |
|---|---|---|
| 2-(4-Morpholinyl)-7-[3-(trifluoromethyl)phenyl]pyrazolo[1,5-a]pyrimidine-3-carbonitrile | 25 | Active |
| 5-Methyl-7-phenyl-2-[4-(phenylmethyl)-1-piperazinyl]pyrazolo[1,5-a]pyrimidine-3-carbonitrile | 25 | Active |
| 2-[4-[(3-Chlorophenyl)methyl]-1-piperazinyl]-7-phenylpyrazolo[1,5-a]pyrimidine-3-carbonitrile | 25 | Active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, pg 732 (April 1977) and H. Mohler, et al., Science, 198, pg 849 (1977) was employed.

Male albino rats (Wistar strain, weighing 150–200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen (−20° C.) until time of use. Frozen $P_2$ preparations were thawed and resuspended in four times the original homogenizing volume at time of assay.

The binding assay consisted of 300 μl of the $P_2$-fraction suspension (0.2–0.4 mg protein), 100 μl of test drug and 100 μl of $^3$H-diazepam (1.5 nM, final concentration) or $^3$H-flunitrazepam (1.0 nM, final concentration) which was added to 1.5 ml of 50 mM Tris.HCl (pH 7.4). Nonspecific binding controls and total binding controls received 100 μl of diazepam (3 μM final concentration) and 100 μl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°–60° C. for 30 minutes, 10 ml of Beckman Ready-Solve HP was added and the radioactivity determined in a Beckman Scintillation Counter.

Inhibition of binding was calculated by the difference between total binding and binding in the presence of test compound, divided by the total binding, ×100.

The results of this test on representative compounds of this invention appear in Table III.

TABLE III

Inhibition of the Binding of $^3$H—Benzodiazepine to Brain-Specific Receptors of Rats

| Compound | % Inhibition |
|---|---|
| 2-(4-Morpholinyl)-7-[3-(trifluoromethyl)phenyl]pyrazolo[1,5-a]pyrimidine-3-carbonitrile | 34 |
| 2-(4-Methyl-1-piperazinyl)-7-[3-(trifluoromethyl)phenyl]pyrazolo[1,5-a]pyrimidine-3-carbonitrile | 34 |
| 2-(4-Phenyl-1-piperazinyl)-7-[3-(trifluoromethyl)phenyl]pyrazolo[1,5-a]pyrimidine-3-carbonitrile | 34 |
| 2-[4-(2-Pyridinyl)-1-piperazinyl]-7-[3-(trifluoromethyl)phenyl]pyrazolo[1,5-a]pyrimidine-3-carbonitrile | 34 |
| 2-(1-Piperidinyl)-7-[3-(trifluoromethyl)phenyl]pyrazolo[1,5-a]pyrimidine-3-carbonitrile | 43 |
| 7-(4-Chlorophenyl)-2-(4-morpholinyl)pyrazolo[1,5-a]pyrimidine-3-carbonitrile | 43 |
| 7-(4-Chlorophenyl)-2-[4-(phenylmethyl)-1-piperazinyl]pyrazolo[1,5-a]pyrimidine-3-carbonitrile | 43 |
| 7-Phenyl-2-[4-(phenylmethyl)-1-piperazinyl]pyrazolo[1,5-a]pyrimidine-3-carbonitrile | 43 |
| 2-[4-(4-Phenoxybutyl)-1-piperazinyl]-7-[3-(trifluoromethyl)phenyl]pyrazolo[1,5-a]pyrimidine-3-carbonitrile | 26 |
| 2-[4-(2-Hydroxyethyl)-1-piperazinyl]-7-[3-(trifluoromethyl)phenyl]pyrazolo[1,5-a]pyrimidine-3-carbonitrile | 41 |
| 7-(3-Pyridinyl)-2-[4-(2-pyridinyl)-1-piperazinyl]pyrazolo[1,5-a]pyrimidine-3-carbonitrile | 40 |
| 2-(1-Piperidinyl)-7-(3-pyridinyl)pyrazolo[1,5-a]pyrimidine-3-carbonitrile | 10 |
| 2-[4-(4-Phenoxybutyl)-1-piperazinyl]-7-(3-pyridinyl)pyrazolo[1,5-a]pyrimidine-3-carbonitrile | 14 |
| 2-[4-(2-Hydroxyethyl)-1-piperazinyl]-7-(3-pyridinyl)pyrazolo[1,5-a]pyrimidine-3-carbonitrile | 33 |
| 2-[4-(Phenylmethyl)-1-piperazinyl]-7-[3-(trifluoromethyl)phenyl]pyrazolo[1,5-a]pyrimidine-3-carboxamide | 25 |
| 2-[4-(Phneylmethyl)-1-piperidinyl]-7-[3-(trifluoromethyl)phenyl]pyrazolo[1,5-a]pyrimidine-3-carbonitrile | 14 |
| 2-[4-[(3-Chlorophenyl)methyl]-1-piperazinyl]-7-(3-pyridinyl)pyrazolo[1,5-a]pyrimidine-3-carbonitrile | 46 |
| 2-[4-[(3-Chlorophenyl)methyl]-1-piperazinyl]-7-[3-(trifluoromethyl)phenyl]pyrazolo[1,5-a]pyrimidine-3-carbonitrile | 12 |
| 2-[4-[(4-Methoxyphenyl)methyl]-1-piperazinyl]-7-[3-(trifluoromethyl)phenyl]pyrazolo[1,5-a]pyrimidine-3-carbonitrile | 33 |
| 2-[4-[(4-Chlorophenyl)methyl]-1-piperazinyl]-7-[3-(trifluoromethyl)phenyl]pyrazolo[1,5-a]pyrimidine-3-carbonitrile | 18 |
| 2-[4-[(3-Methoxyphenyl)methyl]-1-piperazinyl]-7-(3-pyridinyl)pyrazolo[1,5-a]pyrimidine-3-carbonitrile | 15 |
| 2-[4-[(2,6-Dichlorophenyl)methyl]-1-piperazinyl]-7-[3-(trifluoromethyl)phenyl]pyrazolo[1,5-a]pyrimidine-3-carbonitrile | 18 |
| | 22 |

Certain of the novel compounds of the present invention possess the ability to enhance neural function in warm-blooded animals affected by behavioral neurological problems, including the cognitive deterioration associated with decreased neural function which occurs with cerebal insufficiency, aging, dementia and similar conditions.

A useful in vivo test that demonstrates the ability of the test compounds relative to a known parasympathomimetric agent (physostigmine) is the Hypoxic Survival Test. This test shows the enhanced survival of test animals in a hypoxic environment when treated with drug as compared to saline treated control animals with no drug.

Groups of 20 Royal Hart mice (6 weeks of age) are injected intraperitoneally with 10, 50 or 100 mg/kg of test compound 30 minutes prior to placing them in a hypoxic mixture (10% oxygen in 90% carbon dioxide) and measuring survival after 5 minutes.

A separate group of 20 mice is injected intraperitoneally with saline solution (0.01 cc/g of body weight) and processed as described above.

Still another group of 20 mice is injected intraperitoneally with 0.125 mg/kg of physostigmine and processed as described above.

Extensive testing of controls has demonstrated that only 5–20% of saline treated mice survive after a 5 minute exposure, whereas 60–80% of the physostigmine treated mice survive.

Results of this test on representative compounds of the present invention appear in Table IV.

TABLE IV

Hypoxic Survival Test

| Compound | Dose mg/kg | % Survivors |
|---|---|---|
| 2-[4-(Phenylmethyl)-1-piperazinyl]-7-(3-pyridinyl)pyrazolo[1,5-a]pyrimidine-3-carbonitrile | 50 | 40 |
| 2-[4-(Phenylmethyl)-1-piperazinyl]-7-[3-(trifluoromethyl)phenyl]pyrazolo[1,5-a]pyrimidine-3-carbonitrile | 50 | 52 |
| 7-(3-Chlorophenyl)-2-[4-(phenylmethyl)-1-piperazinyl]pyrazolo[1,5-a]pyrimidine-3-carbonitrile | 50 | 47 |
| 2-(1-Piperidinyl)-7-(3-pyridinyl)pyrazolo[1,5-a]pyrimidine-3-carbonitrile | 100 | 45 |
| 7-(3-Pyridinyl)-2-(4-thiomorpholinyl)pyrazolo[1,5-a]pyrimidine-3-carbonitrile | 100 | 50 |
| 2-[4-(2-Hydroxyethyl)-1-piperazinyl]-7-[3-(trifluoromethyl)phenyl]pyrazolo[1,5-a]pyrimidine-3-carbonitrile | 10 | 45 |

Another in vivo test associated with decreased neural function in mammals is the Passive Avoidance Anoxic Induced Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Swiss-Webster, middle-aged mice (9 months of age) are placed singly in the front chamber of a 2-chamber box and are allowed to voluntarily cross into the rear chamber. As soon as the mouse enters the rear chamber, a guillotine door automatically traps the animal and a mild electric shock (0.4 mA for 4 seconds) is delivered to its feet. Following the foot shock, the mice are initially placed in an anoxic environment (0% oxygen) for 12 seconds, which quickly induces unconsciousness. They are then placed in a hypoxic environment (15% oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 10–100 mg/kg, 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30% over saline control scores is considered active. The result of this test on a representative compound of the present invention appears in Table V.

TABLE V

Passive Avoidance Anoxic Induced Amnesia Test

| Compound | Dose mg/kg | % Improvement |
|---|---|---|
| 2-[4-(Phenylmethyl)-1-piperazinyl]-7-[3-(trifluoromethyl)phenyl]pyrazolo[1,5-a]pyrimidine-3-carbonitrile | 100 | 44 |

The novel compounds of the present invention have been found to be highly useful for lowering elevated blood pressure in mammals when administered in amounts ranging from about 0.5 mg to about 100 mg/kg of body weight per day. A preferred dosage regimen for optimum results would be from about 1 mg to about 25 mg/kg of body weight per day, and such dosage units are employed that a total of from about 70 mg to about 1.75 g of the active compound for a subject of about 70 kg of body weight are administered in a 24 hour period.

The novel compounds of the present invention have been found to be useful for meliorating anxiety in mammals when administered in amounts ranging from about 0.5 mg to about 100 mg/kg of body weight per day. A preferred dosage regimen for optimum results would be from about 1 mg to about 30 mg/kg of body weight per day, and such dosage units are employed that a total of from about 70 mg to about 2.1 g of the active compound for a subject of about 70 kg of body weight are administered in a 24 hour period.

Some of the compounds of the present invention have been found to be useful as agents for the treatment of cognitive and related neural behavioral problems in mammals when administered in amounts ranging from about 1 mg to about 200 mg/kg of body weight per day. A preferred dosage regimen for optimum results would be from about 5 mg to about 50 mg/kg of body weight per day and such dosage units are employed that a total of from about 350 mg to about 3.5 g of the active compound for a subject of about 70 kg of body weight are administered in a 24 hour period.

The hereinabove described dosage regimens for lowering elevated blood pressure, meliorating anxiety and treating neural behavioral problems in mammals may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can a be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following specific examples.

EXAMPLE 1

3-Amino-5-(4-phenylmethyl-1-piperazinyl)-4-pyrazolecarbonitrile

A mixture of 4.25 g (0.025 moles) of [bis(methylthio)methylene]malononitrile [K. A. Jensen and L. Hendriksen, *Acta Chem. Scand.*, 22(4), 1107 (1968)] and 4.7 g (0.025 moles) of 1-benzylpiperazine in 100 ml of acetonitrile was stirred at reflux for 5 hours with evolution of methanethiol. Then 1.31 g (0.025 moles) of hydrazine hydrate was added and the solution was stirred at reflux for 16 hours, again with evolution of methanethiol. The reaction mixture was clarified while hot with activated charcoal and filtered through diatomaceous earth. The filtrate was cooled at −10° C. and a white precipitate developed. The precipitate was collected by filtration, washed with 50 ml of cold acetonitrile, air dried, then dried in vacuo at 60° C. and gave 4.5 g of crude product. The material was recrystallized from 150 ml of 2-propanol, cooled at −10° C. and gave 2.8 g of the desired product as a white solid, mp 157°–158° C.

EXAMPLES 2–20

Additional intermediate compounds listed in Table VI which are used to prepare the novel pyrazolo[1,5-a]pyrimidines of the present invention were prepared in the manner described in Example 1, by reacting equimolar amounts of [bis(methylthio)methylene]-malononitrile with a compound of the general structure (III) in scheme A, described in our related U.S. Pat. No. 4,421,753 or with a compound such as morpholine, thiomorpholine, piperidine or 4-phenylmethylpiperidine at the reflux temperature for 2–20 hours in acetonitrile, giving a solution of a compound of the general structure (IV) in Scheme A which is refluxed with hydrazine hydrate in the solvent for 1–18 hours to obtain the desired intermediate compound.

Certain of the intermediate compounds have been disclosed as being useful as hypotensive agents and/or as intermediates to prepare certain pyrazolo[1,5-a]pyrimidines encompassed by the present invention.

TABLE VI

3-Amino-5-substituted pyrazole-3-carbonitrile Intermediates

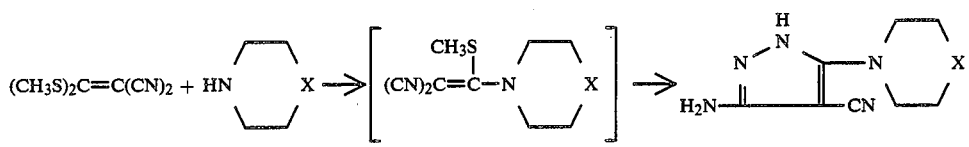

| Ex. | Compound | X | Description | MP °C. |
|---|---|---|---|---|
| 2 | 3-Amino-5-[4-[(3,4-dichlorophenyl)-methyl]-1-piperazinyl]-1$\underline{H}$—pyrazole-4-carbonitrile | \N—CH₂—C₆H₃Cl₂ | White Solid | 176–178 |
| 3 | 3-Amino-5-[4-(2-furanylmethyl)-1-piperazinyl]-1$\underline{H}$—pyrazole-4-carbonitrile | \N—CH₂—(2-furanyl) | White Solid | 138–140 |
| 4 | 5-Amino-3-[4-(3-phenoxypropyl)-1-piperazinyl]-1$\underline{H}$—pyrazole-4-carbonitrile | \N—CH₂CH₂CH₂—O—C₆H₅ | Cream Colored Crystals | 125–127 (dec) |
| 5 | 5-Amino-3-[4-(4-phenoxybutyl)-1-piperazinyl]-1$\underline{H}$—pyrazole-4-carbonitrile | \N—CH₂(CH₂)₂CH₂—O—C₆H₅ | Cream Colored Crystals | 109–112 |
| 6 | 5-Amino-3-[4-(2-phenoxyethyl)-1-piperazinyl]-1$\underline{H}$—pyrazole-4-carbonitrile | \N—CH₂CH₂—O—C₆H₅ | Off-white Crystals | 147–149 (dec) |
| 7 | 3-Amino-5-[4-(3-phenyl-2-propenyl)-1-piperazinyl]-1$\underline{H}$—pyrazole-4-carbonitrile | \N—CH₂CH=CH—C₆H₅ | White Solid | 216–218 |
| 8 | 3-Amino-5-(4-morpholinyl)-1$\underline{H}$—pyrazolo-4-carbonitrile | \O/ | White Solid | 197–199 |
| 9 | 3-Amino-5-(4-methyl-1-piperazinyl)-1$\underline{H}$—pyrazole-4-carbonitrile | \N—CH₃ | White Solid | 205–208 |

TABLE VI-continued

3-Amino-5-substituted pyrazole-3-carbonitrile Intermediates

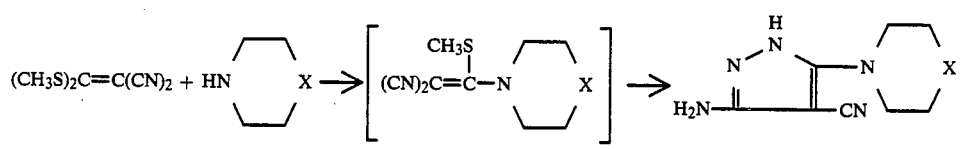

| Ex. | Compound | X | Description | MP °C. |
|-----|----------|---|-------------|--------|
| 10 | 3-Amino-5-(4-phenyl-1-piperazinyl)-1H—pyrazole-4-carbonitrile | >N—C₆H₅ (N-phenyl) | White Solid | 166–168 |
| 11 | 3-Amino-5-[4-(2-pyridinyl)-1-piperazinyl]-1H—pyrazole-4-carbonitrile | >N—(2-pyridinyl) | White Solid | 180–182 |
| 12 | 3-Amino-5-(1-piperidinyl)-1H—pyrazole-4-carbonitrile | >CH₂ | White Solid | 135–137 |
| 13 | 3-Amino-5-(4-thiomorpholinyl)-1H—pyrazole-4-carbonitrile | >S | White Solid | 130–132 |
| 14 | 3-Amino-5-[4-(2-hydroxyethyl)-1-piperazinyl]-1H—pyrazole-4-carbonitrile | >N—CH₂CH₂—OH | White Solid | 174–176 |
| 15 | 3-Amino-5-[4-(phenylmethyl)-1-piperidinyl]-1H—pyrazole-4-carbonitrile | >CH—CH₂—C₆H₅ | Off-White Crystals | 150–153 |
| 16 | 3-Amino-5-[4-[(3-chlorophenyl)methyl]-1-piperazinyl]-1H—pyrazole-4-carbonitrile | >N—CH₂—C₆H₄—Cl (3-Cl) | White Crystals | 162–165 |
| 17 | 3-Amino-5-[4-[(2,6-dichlorophenyl)methyl]-1-piperazinyl]-1H—pyrazole-4-carbonitrile | >N—CH₂—C₆H₃Cl₂ (2,6-di-Cl) | White Crystals | 206–212 |
| 18 | 3-Amino-5-[4-[(4-methoxyphenyl)methyl]-1-piperazinyl]-1H—pyrazole-4-carbonitrile | >N—CH₂—C₆H₄—OCH₃ (4-OCH₃) | White Crystals | 223–228 |
| 19 | 3-Amino-5-[4-[(3-methoxyphenyl)methyl]-1-1-piperazinyl]-1H—pyrazole-4-carbonitrile | >N—CH₂—C₆H₄—OCH₃ (3-OCH₃) | White Crystals | 185–188 |
| 20 | 3-Amino-5-[4-[(4-chlorophenyl)methyl]-1-piperazinyl]-1H—pyrazole-4-carbonitrile | >N—CH₂—C₆H₄—Cl (4-Cl) | White Crystals | 184–187 |

EXAMPLE 21

2-(4-Phenylmethyl-1-piperazinyl)-7-(4-pyridyl)-pyrazolo[1,5-a]pyrimidine-3-carbonitrile A mixture of 2.2 g of 3-amino-5-(4-phenylmethyl-1-piperazinyl)-4-pyrazolecarbonitrile (Example 1) and 1.37 g of 3-dimethylamino-1-(4-pyridyl)-2-propen-1-one U.S. Pat. No. 4,281,000, Example 63) in 25 ml of glacial acetic acid was refluxed for 6 hours. The solution was taken to dryness in vacuo. The residue was partitioned between saturated sodium bicarbonate and dichloromethane (1:2). The dichloromethane layer was separated, dried over anhydrous sodium sulfate and filtered through a short column of magnesium silicate. The effluent was refluxed on a steam bath with the gradual addition of hexane until turbidity was noted. After cooling, the precipitate was collected by filtration. The solid was recrystallized from dichloromethane/hexane and gave 1.65 g of the product of the Example as very pale yellow crystals, mp 193°–194° C.

EXAMPLES 22–55

Additional examples of pyrazolo[1,5-a]pyrimidines which are listed in Table VII were prepared in the manner described in Example 21, by reacting equimolar amounts of an intermediate compound (prepared as hereinabove described) and a 3-dimethylamino-1-(aryl, substituted aryl, or heteroaryl)-2-propen-1-one (prepared as described in U.S. Pat. Nos. 4,281,000 and 4,209,621) in 25–100 ml of refluxing glacial acetic acid for 2–20 hours.

TABLE VII

Pyrazolo[1,5-a]pyrimidines

| Ex. | Precursor | Product | $R_3$ | X | Description | MP °C. |
|---|---|---|---|---|---|---|
| 22 | Ex. 2 | 2-[4-[(3,4-Dichlorophenyl)methyl]-1-piperazinyl]-7-(4-pyridinyl)pyrazolo[1,5-a]pyrimidine-3-carbonitrile | 4-pyridyl | >N—CH₂—C₆H₃(Cl)₂ (3,4-dichlorophenyl) | Yellow Solid | 177–179 |
| 23 | Ex. 1 | 2-[4-Phenylmethyl)-1-piperazinyl]-7-(3-pyridinyl)pyrozolo[1,5-a]pyrimidine-3-carbonitrile | 3-pyridyl | >N—CH₂—C₆H₅ | Off-White Crystals | 173–175 |
| 24 | Ex. 1 | 2-[4-(Phenylmethyl)-1-piperazinyl]-7-[3-(trifluoromethyl)phenyl]pyrazolo[1,5-a]pyrimidine-3-carbonitrile | 3-(trifluoromethyl)phenyl | >N—CH₂—C₆H₅ | Pale Yellow Prisms | 185–186 |
| 25 | Ex. 4 | 2-[4-(3-Phenoxypropyl)-1-piperazinyl]-7-(4-pyridinyl)pyrazolo-[1,5-a]pyrimidine-3-carbonitrile | 4-pyridyl | >N—CH₂CH₂CH₂O—C₆H₅ | Yellow Crystals | 171–172 |
| 26 | Ex. 6 | 2-[4-(2-Phenoxyethyl)-1-piperazinyl]-7-(4-pyridinyl)pyrazolo-[1,5-a]pyrimidine-3-carbonitrile | 4-pyridyl | >N—CH₂CH₂O—C₆H₅ | Yellow Crystals | 171–173 |
| 27 | Ex. 3 | 2-[4-(2-Furanylmethyl)-1-piperazinyl]-7-(4-pyridinyl)pyrazolo-[1,5-a]pyrimidine-3-carbonitrile | 4-pyridyl | >N—CH₂-(2-furanyl) | Yellow Crystals | 174–175 |
| 28 | Ex. 7 | 2-[4-(3-Phenyl-2-propenyl)-1-piperazinyl]-7-(4-pyridinyl)pyrazolo-[1,5-a]pyrimidine-3-carbonitrile | 4-pyridyl | >N—CH₂CH=CH—C₆H₅ | Tan Solid | 202–204 |

TABLE VII-continued

Pyrazolo[1,5-a]pyrimidines

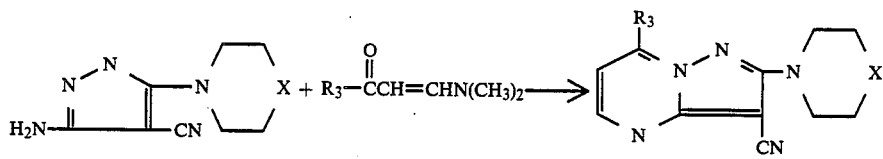

| Ex. | Precursor | Product | R₃ | X | Description | MP °C. |
|---|---|---|---|---|---|---|
| 29 | Ex. 8 | 2-(4-Morpholinyl)-7-[3-(trifluoromethyl)phenyl]-pyrazolo[1,5-a]-pyrimidine-3-carbonitrile | 3-CF₃-C₆H₄ | -O- (morpholine) | Light Yellow Solid | 185–187 |
| 30 | Ex. 9 | 2-(4-Methyl-1-piperazinyl)-7-[3-(trifluoromethyl)phenyl]pyrazolo[1,5-a]pyrimidine-3-carbonitrile | 3-CF₃-C₆H₄ | N—CH₃ | Yellow Solid | 132–134 |
| 31 | Ex. 10 | 2-(4-Phenyl-1-piperazinyl)-7-[3-(triflurormethyl)-phenyl]pyrazolo-[1,5-a]pyrimidine-3-carbonitrile | 3-CF₃-C₆H₄ | N—C₆H₅ | Light Yellow Solid | 193–195 |
| 32 | Ex. 11 | 2-[4-(2-Pyridinyl)-1-piperazinyl]-7-[3-(trifluoromethyl)phenyl]pyrazolo[1,5-a]pyrimidine-3-carbonitrile | 3-CF₃-C₆H₄ | N—(2-pyridinyl) | Yellow Solid | 189–191 |
| 33 | Ex. 12 | 2-(1-Piperidinyl)-7-[3-(trifluoromethyl)phenyl]-pyrazolo[1,5-a]-pyrimidine-3-carbonitrile | 3-CF₃-C₆H₄ | CH₂ | Yellow Solid | 172–174 |
| 34 | Ex. 8 | 7-(4-Chlorophenyl-2-(4-morpholinyl)-pyrazolo[1,5-a]-pyrimidine-3-carbonitrile | 4-Cl-C₆H₄ | -O- (morpholine) | Light Yellow Solid | 240–242 |
| 35 | Ex. 1 | 7-(4-Chlorophenyl)-2-[4-(phenylmethyl)-1-piperazinyl]pyrazolo-[1,5-a]pyrimidine-3-carbonitrile | 4-Cl-C₆H₄ | N—CH₂—C₆H₅ | Tan Solid | 153–157 |
| 36 | Ex. 1 | 7-Phenyl-2-[4-(phenylmethyl)-1-piperazinyl]-pyrazolo[1,5-a]-pyrimidine-3-carbonitrile | C₆H₅ | N—CH₂—C₆H₅ | Yellow Solid | 194–196 |
| 37 | Ex. 1 | 7-(3-Chlorophenyl)-2-[4-(phenylmethyl)-1-piperazinyl]pyrazolo-[1,5-a]pyrimidine-3-carbonitrile | 3-Cl-C₆H₄ | N—CH₂—C₆H₅ | Light Yellow Solid | 118–120 |

TABLE VII-continued
Pyrazolo[1,5-a]pyrimidines

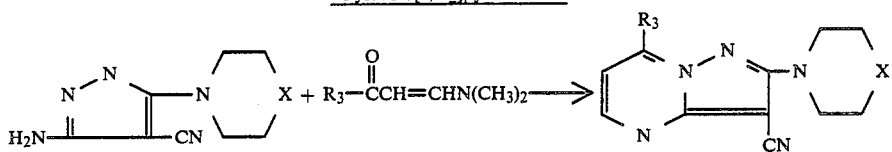

| Ex. | Precursor | Product | R3 | X | Description | MP °C. |
|---|---|---|---|---|---|---|
| 38 | Ex. 5 | 2-[4-(4-Phenoxybutyl)-1-piperazinyl]-7-[3-(trifluoromethyl)phenyl]pyrazolo[1,5-a]pyrimidine-3-carbonitrile | F3C-phenyl | N—CH2(CH2)2CH2O-phenyl | Yellow Solid | 125–127 |
| 39 | Ex. 13 | 2-(4-Thiomorpholinyl)-7-[3-(triflurormethyl)phenyl]pyrazolo[1,5-a]pyrimidine-3-carbonitrile | F3C-phenyl | S | Yellow Solid | 147–150 |
| 40 | Ex. 14 | 2-[4-(2-Hydroxyethyl)-1-piperazinyl]-7-[3-(trifluoromethyl)phenyl]pyrazolo[1,5-a]pyrimidine-3-carbonitrile | F3C-phenyl | N—CH2CH2—OH | Yellow Solid | 118–120 |
| 41 | Ex. 11 | 7-(3-Pyridinyl)-2-[4-(2-pyridinyl)-1-piperazinyl]-pyrazolo[1,5-a]-pyrimidine-3-carbonitrile | 3-pyridinyl | N-(2-pyridinyl) | Yellow Solid | 248–250 |
| 42 | Ex. 12 | 2-(1-Piperidinyl)-7-(3-pyridinyl)-pyrazolo[1,5-a]-pyrimidine-3-carbonitrile | 3-pyridinyl | CH2 | Yellow Solid | 168–170 |
| 43 | Ex. 5 | 2-[4-(4-Phenoxybutyl)-1-piperazinyl]pyrazolo[1,5-a]pyrimidine-3-carbonitrile | 3-pyridinyl | N—CH2(CH2)2CH2—O-phenyl | Yellow Solid | 98–100 |
| 44 | Ex. 13 | 7-(3-Pyridinyl)-2-(4-thiomorpholinyl)pyrazolo[1,5-a]pyrimidine-3-carbonitrile | 3-pyridinyl | S | Yellow Solid | 195–198 |
| 45 | Ex. 14 | 2-[4-(2-Hydroxyethyl)-1-piperazinyl]-7-(3-pyridinyl)pyrazolo-[1,5-a]pyrimidine-3-carbonitrile | 3-pyridinyl | N—CH2CH2—OH | Yellow Solid | 104–108 |
| 46 | Ex. 15 | 2-[4-(Phenylmethyl)-1-piperidinyl]-7-[3-(trifluoromethyl)phenyl]pyrazolo[1,5-a]pyrimidine-3-carbonitrile | F3C-phenyl | CH—CH2-phenyl | Yellow Solid | 160–162 |
| 47 | Ex. 16 | 2-[4-[(3-Chlorophenyl)methyl]-1-piperazinyl]-7-(3-pyridinyl)pyrazolo[1,5-a]pyrimidine-3-carbonitrile | 3-pyridinyl | N—CH2-(3-Cl-phenyl) | Yellow Solid | 122–124 |

TABLE VII-continued
Pyrazolo[1,5-a]pyrimidines

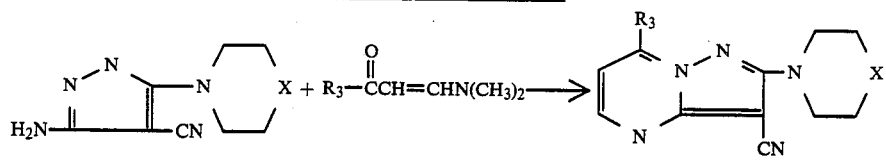

| Ex. | Precursor | Product | R₃ | X | Description | MP °C. |
|---|---|---|---|---|---|---|
| 48 | Ex. 16 | 2-[4-[(3-Chlorophenyl)methyl]-1-piperazinyl]-7-[3-(trifluoromethyl)phenyl]pyrazolo-[1,5-a]pyrimidine-3-carbonitrile | 3-(F₃C)C₆H₄– | –N(CH₃)–CH₂–C₆H₄–Cl (4-Cl) | Yellow Solid | 171–173 |
| 49 | Ex. 18 | 2-[4-[(4-Methoxyphenyl)methyl]-1-piperazinyl]-7-[3-(trifluoromethyl)phenyl]-pyrazolo[1,5-a]-pyrimidine-3-carbonitrile | 3-(F₃C)C₆H₄– | –N(CH₃)–CH₂–C₆H₄–OCH₃ (4-OCH₃) | Yellow Solid | 134–136 |
| 50 | Ex. 20 | 2-[4-[(4-Chlorophenyl)methyl]-1-piperazinyl]-7-(3-pyridinyl)-pyrazolo[1,5-a]-pyrimidine-3-carbonitrile | 3-pyridinyl | –N(CH₃)–CH₂–C₆H₄–Cl (4-Cl) | Yellow Solid | 176–178 |
| 51 | Ex. 20 | 2-[4-[(4-Chlorophenyl)methyl]-1-piperazinyl]-7-[3-(trifuloromethyl)phenyl]pyrazolo[1,5-a]pyrimidine-3-carbonitrile | 3-(F₃C)C₆H₄– | –N(CH₃)–CH₂–C₆H₄–Cl (4-Cl) | Yellow Solid | 167–169 |
| 52 | Ex. 19 | 2-[4-[(3-Methoxyphenyl)methyl]-1-piperazinyl]-7-[3-(trifluoromethyl)phenyl]pyrazolo-[1,5-a]pyrimidine-3-carbonitrile | 3-(F₃C)C₆H₄– | –N(CH₃)–CH₂–C₆H₄–OCH₃ (3-OCH₃) | Yellow Solid | 134–135 |
| 53 | Ex. 17 | 2-[4-[(2,6-Dichlorophenyl)methyl]-1-piperazinyl]-7-(3-pyridinyl)pyrazolo[1,5-a]pyrimidine-3-carbonitrile | 3-pyridinyl | –N(CH₃)–CH₂–C₆H₃–Cl₂ (2,6-Cl₂) | Yellow Solid | 190–192 |
| 54 | Ex. 17 | 2-[4-[(2,6-Dichlorophenyl)methyl]-1-piperazinyl]-7-[3-(trifluoromethyl)phenyl]pyrazolo[1,5-a]pyrimidine-3-carbonitrile | 3-(F₃C)C₆H₄– | –N(CH₃)–CH₂–C₆H₃–Cl₂ (2,6-Cl₂) | Yellow Solid | 136–138 |
| 55 | Ex. 16 | 2-[4-[(3-Chlorophenyl)methyl]-1-piperazinyl]-7-phenylpyrazolo-[1,5-a]pyrimidine-3-carbonitrile | C₆H₅– | –N(CH₃)–CH₂–C₆H₄–Cl (3-Cl) | Beige Solid | 108–110 |

EXAMPLE 56

2-[4-(Phenylmethyl)-1-piperazinyl]-7-(4-pyridinyl)-pyrazolo[1,5-a]pyrimidine-3-carboxamide A 4.0 g amount of 3-amino-5-(4-phenylmethyl-1-piperazinyl)-4-pyrazolecarbonitrile (prepared as described in Example 1) was added to 25 ml of concentrated sulfuric acid. The mixture was stirred and heated on a steam bath at 90°–95° C. for 3 hours. Then was allowed to stand at ambient temperature for 16 hours. The mixture was poured into 300 ml of ice/water. The solution was made basic with concentrated ammonium hydroxide and cooled at 5° C. giving a tacky precipitate. The aqueous phase was decanted and the residue was dissolved in 200 ml of boiling ethanol. The solution was clarified hot with activated charcoal, then filtered. The filtrate was concentrated to 100 ml, water was added and the mixture was heated on the steam bath until turbidity was noted. The mixture was cooled at −10° C. The precipitate was collected by filtration, washed with 30 ml of cold 50% ethanol, air dried, then dried in vacuo at 60° C. and gave 2.0 g of the desired product as yellow crystals, mp 205°–206° C.

EXAMPLE 57

2-[4-(Phenylmethyl)-1-piperazinyl]-7-(4-pyridinyl)-5-(trifluoromethyl)pyrazolo[1,5-a]pyrimidine-3-carbonitrile A mixture of 3.9 g (0.014 moles) of 4,4,4-trifluoro-1-(4-pyridyl)-1,3-butanedione (U.S. Pat. No. 3,200,128), 3.9 g (0.014 moles) of 3-amino-5-(4-phenylmethyl-1-piperazinyl)-4-pyrazolecarbonitrile (prepared as described in Example 1) and 100 ml of glacial acetic acid was stirred at reflux for 16 hours.

The resulting solution was taken to dryness in vacuo. The residue was partitioned between 100 ml of saturated sodium bicarbonate solution and 200 ml of dichloromethane. The organic layer was separated, dried over magnesium sulfate and passed through a short column of magnesium silicate. The filtrate was diluted with 200 ml of hexane. This solution was concentrated to about 125 ml, then cooled at −10° C. The precipitate formed was collected by filtration, washed with hexane, air dried, then dried in vacuo and gave 2.4 g of the product of the Example as a yellow solid, mp 147°–149° C.

EXAMPLE 58

5-Methyl-2-[4-(phenylmethyl)-1-piperazinyl]-7-(4-pyridinyl)pyrazolo[1,5-a]pyrimidine-3-carbonitrile A mixture of 4.8 g (0.03 moles) of 1-(4-pyridyl)-1,3-butanedione [J. Chem. Soc. (1950) p 1680], 8.4 g (0.03 moles) of 3-amino-5-(4-phenylmethyl-1-piperazinyl)-4-pyrazolecarbonitrile (prepared as described in Example 1) and 100 ml of glacial acetic acid was stirred at reflux for 18 hours.

The resulting solution was evaporated in vacuo and gave an oil. The residue was partitioned between 100 ml of saturated sodium bicarbonate and 200 ml of dichloromethane. The organic layer was separated, dried over magnesium sulfate and passed through a short column of magnesium silicate. The eluate was heated to boiling on a steam bath and 200 ml of hexane was added. The solution was concentrated by heating until a precipitate began to form. The mixture was then cooled at −10° C. and filtered. The precipitate was washed with hexane. The filtrate and wash was combined, concentrated to turbidity, cooled at −10° C. and filtered to collect the solid which was dried and gave 3.9 g of the desired product as a yellow solid, mp 179°–180° C.

EXAMPLE 59

5-Methyl-7-phenyl-2-[4-(phenylmethyl)-1-piperazinyl]-pyrazolo[1,5-a]pyrimidine-3-carbonitrile A mixture of 2.9 g (0.018 moles) of 1-phenyl-1,3-butanedione, 5.0 g (0.018 moles) of 3-amino-5-(4-phenylmethyl-1-piperazinyl)-4-pyrazolecarbonitrile (prepared as described in Example 1) and 25 ml of glacial acetic acid was refluxed for 4 hours. The reaction mixture was evaporated in vacuo and gave a thick oil. The oil was dissolved in dichloromethane and partitioned with saturated sodium bicarbonate. The organic layer was separated, dried over anhydrous sodium sulfate and passed through magnesium silicate. The solution was evaporated in vacuo and gave a yellow solid which was recrystallized from isopropanol and cyclohexane and gave 5.5 g of the desired product as a light yellow solid, mp 160°–164° C.

EXAMPLE 60

2-[4-(Phenylmethyl)-1-piperazinyl]-7-[3-(trifluoromethyl)phenyl]pyrazolo[1,5-a]pyrimidine-3-carboxamide A mixture of 7.0 g of 2-[4-(phenylmethyl)-1-piperazinyl]-7-[3-(trifluoromethyl)phenyl]pyrazolo[1,5-a]pyrimidine-3-carbonitrile (prepared as described in Example 24) and 50 ml of concentrated sulfuric acid was stirred at room temperature for 5 hours. The yellow solution was poured into ice/water. The precipitate formed was collected and washed with water, then dried in vacuo. The material was recrystallized from acetonitrile, collected and dried and gave 4.8 g of the product of the Example as a yellow solid, mp 252°–254° C.

EXAMPLE 61

N-[(Dimethylamino)methylene]-2-[4-(phenylmethyl)-1-piperazinyl]-7-[3-(trifluoromethyl)phenyl]pyrazolo-[1,5-a]pyrimidine-3-carboxamide A 3.65 g (0.076 mole) amount of the product of Example 60 and 20 ml of N,N-dimethylformamide dimethyl acetal was heated in an oil bath at 130° C. for 2 hours. The mixture was allowed to stand at room temperature for 16 hours then was evaporated in vacuo to give an oil. The oil was dissolved in dichloromethane and hexane was added to separate some solid which was removed by filtration. The filtrate was evaporated in vacuo and gave an oil. An additional 40 ml of N,N-dimethylformamide dimethyl acetal was added to the oil and the mixture was heated at 120° C. for 2 hours. The resulting oil was dissolved in dichloromethane and evaporated in vacuo at 40° C. and gave 3.30 g of solid. The solid was treated with hexane, heating on a steam bath. The solid was collected and dried in vacuo and gave 2.8 g of the desired product as a yellow solid, mp 140°–142° C.

In a like manner when the product of Example 60 is reacted as above with N,N-dimethylacetamide dimethyl acetal, N-[1-(dimethylamino)ethylidene]-2-[4-(phenylmethyl)-1-piperazinyl]-7-[3-(trifluoromethyphenyl]pyrazolo[1,5-a]pyrimidine-3-carboxamide is obtained.

In a like manner when the product of Example 60 is reacted as above with N-N-dimethylbenzamide diethyl acetal, N-[(dimethylamino)phenylmethylene]-2-[4-

(phenylmethyl)-1-piperazinyl]-7-[3-(trifluoromethyl-phenyl)phenyl]pyrazolo[1,5-a]pyrimidine-3-carboxamide is obtained.

EXAMPLE 62

2-[4-[(3-Methoxyphenyl)methyl]-1-piperazinyl]-7-(3-pyridinyl)pyrazolo[1,5-a]pyrimidine-3-carbonitrile, monohydrochloride A mixture of 5.0 g of 3-amino-5-[4-[(3-methoxyphenyl)methyl]-1-piperazinyl]-1H-pyrazole-4-carbonitrile (prepared as described in Example 19) and 2.9 g of 3-dimethylamino-1-(3-pyridyl)-2-propen-1-one (U.S. Pat. No. 4,281,000, Example 1) in 25 ml of glacial acetic acid was heated at reflux for 3 hours. The work procedure of Example 21 was followed to obtain a gummy solid. The solid was dissolved in isopropanol and was treated with 20 ml of 2.9N ethanolic hydrochloric acid. The yellow precipitate formed was collected by filtration, washed with isopropanol and dried in vacuo. The product was recrystallized from ethanol/water and gave 2.5 g of the desired product as a yellow solid, mp >250° C.

EXAMPLE 63

2-[4-[2,6-Dichlorophenyl)methyl]-1-piperazinyl]-7-(4-pyridinyl)pyrazolo[1,5-a]pyrimidine-3-carbonitrile A mixture of 3.5 g (0.01 mole) of 3-amino-5-[4-[(2,6-dichlorophenyl)methyl]-1-piperazinyl]-1H-pyrazole-4-carbonitrile (prepared as described in Example 17) and 1.8 g (0.01 mole) of 3-dimethylamino-1-(4-pyridyl)-2-propen-1-one in 10 ml of glacial acetic acid was heated on a steam bath resulting in some solid being precipitated. The mixture was filtered and the filtrate was diluted with 50 ml of water. The solution was made basic by the addition of 50 ml of 10N sodium hydroxide then was extracted twice with 100 ml of dichloromethane. The combined extract was dried over anhydrous sodium sulfate, then passed through a layer of magnesium silicate. The filtrate was evaporated in vacuo and gave 5.3 of yellow crystals. These crystals were recrystallized from ethyl acetate. The filtrate from this step was allowed to stand and separated a yellow solid. The solid was collected by filtration and gave 500 mg. of the product of the Example, mp 130°-140° C.

We claim:

1. A compound selected from the group consisting of those of the formula:

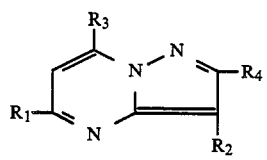

wherein $R_1$ is hydrogen, methyl or trifluoromethyl, $R_2$ is cyano, carbamoyl or moiety of the formula:

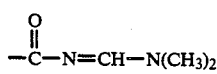

$R_3$ is phenyl, 3-chlorophenyl, 4-chlorophenyl, 3-trifluoromethylphenyl, 3-pyridyl or 4-pyridyl, and $R_4$ is 1-piperidino, 4-benzyl-1-piperidino, 4-thiomorpholino, 4-morpholino or a piperazino moiety of the formula:

wherein $R_5$ is methyl, phenyl, 2-pyridyl, 2-furanylmethyl, 3-phenyl-2-propenyl, benzyl, 3-chlorobenzyl, 4-chlorobenzyl, 3,4-dichlorobenzyl, 2,6-dichlorobenzyl, 3-methoxybenzyl, 4-methoxybenzyl, β-hydroxyethyl, 2-phenoxyethyl, 3-phenoxypropyl or 4-phenoxybutyl with the proviso that when $R_1$ is methyl or trifluoromethyl then $R_3$ is phenyl or 4-pyridyl and $R_4$ is 4-benzyl-1-piperazinyl; and the pharmacologically acceptable acid-addition salts thereof.

2. The compound in accordance with claim 1; 2-(4-phenylmethyl-1-piperazinyl)-7-(4-pyridinyl)pyrazolo[1,5a]pyrimidine-3-carbonitrile.

3. The compound in accordance with claim 1; 2-[4[(3,4-dichlorophenyl)methyl]-1-piperazinyl]-7-(4-pyridinyl)pyrazolo[1,5-a]pyrimidine-3-carbonitrile.

4. The compound in accordance with claim 1; 2-[4-(phenylmethyl)-1-piperazinyl]-7-(3-pyridinyl)-pyrazolo[1,5-a]pyrimidine-3-carbonitrile.

5. The compound in accordance with claim 1; 2-[4-(phenylmethyl)-1-piperazinyl]-7-[3-(trifluoromethyl)-phenyl]pyrazolo[1,5-a]pyrimidine-3-carbonitrile.

6. The compound in accordance with claim 1; 2-[4-(phenylmethyl)-1-piperazinyl]-7-(4-pyridinyl)-pyrazolo[1,5-a]pyrimidine-3-carboxamide.

7. The compound in accordance with claim 1; 2-[4-(phenylmethyl)-1-piperazinyl]-7-(4-pyridinyl)-5-(trifluoromethyl)pyrazolo[1,5-a]pyrimidine-3-carbonitrile.

8. The compound in accordance with claim 1; 2-[4-(3-phenoxypropyl)-1-piperazinyl]-7-(4-pyridinyl)-pyrazolo[1,5-a]pyrimidine-3-carbonitrile.

9. The compound in accordance with claim 1; 2-[4-(2-furanylmethyl)-1-piperazinyl]-7-(4-pyridinyl)-pyrapyrazolo[1,5-a]pyrimidine-3-carbonitrile.

10. The compound in accordance with claim 1; 5-methyl-2-[4-(phenylmethyl)-1-piperazinyl]-7-(4-pyridinyl)pyrazolo[1,5-a]pyrimidine-3-carbonitrile.

11. The compound in accordance with claim 1; 5-methyl-7-phenyl-2-[4-(phenylmethyl)-1-piperazinyl]-pyrazolo[1,5-a]pyrimidine-3-carbonitrile.

12. The compound in accordance with claim 1; 2-(4-thiomorpholinyl)-7-[3-(trifluoromethyl)phenyl]-pyrazolo[1,5-a]pyrimidine-3-carbonitrile.

13. The compound in accordance with claim 1; 2-[4-(phenylmethyl)-1-piperazinyl]-7-[3-(trifluoromethyyl)-phenyl]pyrazolo[1,5-a]pyrimidine-3-carboxamide.

14. The compound in accordance with claim 1; N-[(dimethylamino)methylene]-2-[4-(phenylmethyl)-1-piperazinyl]-7-[3-(trifluoromethyl)phenyl]pyrazolo[1,5-a]pyrimidine-3-carboxamide.

15. The compound in accordance with claim 1; 2-[4-[(4-chlorophenyl)methyl]-1-piperazinyl]-7-[3-(trifluoromethyl)phenyl]pyrazolo[1,5-a]pyrimidine-3-carbonitrile.

16. The compound in accordance with claim 1; 2-[4-[(2,6-dichlorophenyl)methyl]-1-piperazinyl]-7-(4-pyridinyl)pyrazolo[1,5-a]pyrimidine-3-carbonitrile.

17. A method of lowering blood pressure in a mammal which comprises administering to said mammal an effective hypotensive amount of a compound of claim 1.

18. A method of meliorating anxiety in a mammal which comprises administering internally to said mammal an effective anxiolytic amount of a compound of the formula:

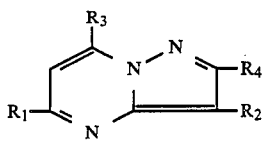

wherein R₁ is hydrogen or methyl, R₂ is cyano or carbamoyl, R₃ is phenyl, 4-chlorophenyl, 3-trifluoromethylphenyl, 4-pyridyl or 3-pyridyl, and R₄ is 1-piperidino, 4-benzyl-1-piperidino, 4-morpholino or a piperazino moiety of the formula:

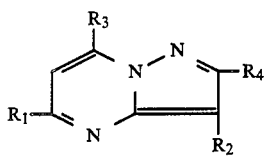

(I)

wherein R₅ is methyl, phenyl, 2-pyridyl, benzyl, 3-chlorobenzyl, 4-chlorobenzyl, 2,6-dichlorobenzyl, 3-methoxybenzyl, 4-methoxybenzyl, β-hydroxyethyl or 4-phenoxybutyl with the proviso that when R₁ is methyl then R₃ is phenyl or 4-pyridyl and R₄ is 4-benzyl-1-piperazinyl; and the pharmacologically acceptable acid-addition salts thereof.

19. A method of treating cognitive and related neural behavioral problems in a mammal which comprises administering internally to said mammal an effective amount of a compound of the formula:

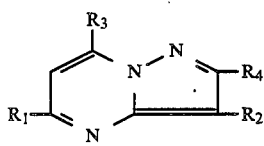

wherein R₁ is hydrogen or trifluoromethyl; R₂ is cyano or carbamoyl; R₃ is phenyl, 3-chlorophenyl, 3-trifluoromethylphenyl, 4-pyridyl or 3-pyridyl and R₄ is 1-piperidino 4-thiomorpholoino or a piperazino moiety of the formula:

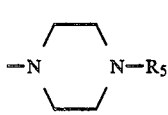

wherein R₅ is benzyl or β-hydroxyethyl with the proviso that when R₁ is trifluoromethyl then R₃ is phenyl or 4-pyridyl and R₄ is 4-benzyl-1-piperazinyl; and the pharmacologically acceptable acid-addition salts thereof.

20. A therapeutic hypotensive composition in dosage unit form useful for lowering elevated blood pressure in mammals consisting of an effective amount of a compound of claim 1 in association with a pharmaceutically acceptable carrier.

21. A therapeutic antianxiety composition in dosage unit form useful for meliorating anxiey in mammals consisting of an effective amount of a compound of the formula:

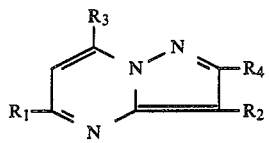

wherein R₁ is hydrogen or methyl, R₂ is cyano or carbamoyl, R₃ is phenyl, 4-chlorophenyl, 3-trifluoromethylphenyl, 3-pyridyl or 4-pyridyl, and R₄ is 1-piperidino, 4-benzyl-1-piperidino, 4-morpholino or a moiety of the formula:

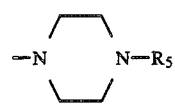

wherein R₅ is methyl, phenyl, 2-pyridyl, benzyl, 3-chlorobenzyl, 4-chlorobenzyl, 2,6-dichlorobenzyl, 3-methoxybenzyl, 4-methoxybenzyl, β-hydroxyethyl or 4-phenoxybutyl with the proviso that when R₁ is methyl then R₃ is phenyl or 4-pyridyl and R₄ is 4-benzyl-1-piperazinyl; and the pharmacologically acceptable acid-addition salts thereof in association with a pharmaceutically acceptable carrier.

22. A therapeutic neurotropic composition in dosage unit form useful for the treatment of cognitive and related neural behavioral problems in mammals consisting of an effective amount of a compound the formula:

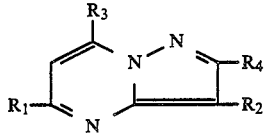

wherein R₁ is hydrogen or trifluoromethyl, R₂ is cyano or carbamoyl, R₃ is phenyl, 3-chlorophenyl, 3-trifluoromethylphenyl, 3-pyridyl or 4-pyridyl, and R₄ is 1-piperidino, 4-morpholino or a moiety of the formula:

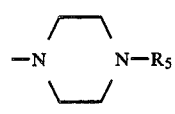

wherein R₅ is benzyl or β-hydroxyethyl with the proviso that when R₁ is trifluoromethyl then R₃ is phenyl or 4-pyridyl and R₄ is 4-benzyl-1-piperazinyl; and the pharmacologically acceptable acid-addition salts thereof in association with a pharmaceutically acceptable carrier.

* * * * *